United States Patent [19]

Inbar et al.

[11] Patent Number: 4,773,268
[45] Date of Patent: Sep. 27, 1988

[54] MULTIPLE TRANSDUCER ULTRASOUND PROBES

[76] Inventors: Dan Inbar; Avraham Bruck; Moshe Epstein, all of c/o Elscint Ltd., P.O. Box 550, Haifa, Israel, 31004

[21] Appl. No.: 914,672

[22] Filed: Oct. 2, 1986

[30] Foreign Application Priority Data

Oct. 4, 1985 [IL] Israel .................................. 76571

[51] Int. Cl.⁴ ............................................. G01N 29/00
[52] U.S. Cl. ................................... 73/625; 73/626; 73/641
[58] Field of Search ............... 254/901, 903, 199; 74/505, 506, 89.22; 73/639, 625, 626, 641; 128/660

[56] References Cited

U.S. PATENT DOCUMENTS

| | | | |
|---|---|---|---|
| 4,149,419 | 4/1979 | Connell, Jr. et al. | 73/639 |
| 4,383,447 | 5/1983 | Kretz | 73/626 |
| 4,476,873 | 10/1984 | Sorenson et al. | 73/625 |
| 4,507,979 | 4/1985 | Zebrowski | 74/506 |
| 4,622,501 | 11/1986 | Eventoff et al. | 128/660 |
| 4,674,514 | 6/1987 | Abbott et al. | 73/626 |

*Primary Examiner*—Stewart J. Levy
*Assistant Examiner*—Robert P. Bell
*Attorney, Agent, or Firm*—Sandler & Greenblum

[57] ABSTRACT

A multi-transducer ultrasound probe including a housing having an ultrasound window with a torquer driven pulley system for positioning and oscillating a selected one of the multi-transducers in the window while activating the selected transducer.

4 Claims, 3 Drawing Sheets

MULTIPLE TRANSDUCER ULTRASOUND PROBES

FIELD OF THE INVENTION

This invention is concerned with ultrasonic imaging apparatus and more particularly ultrasonic imaging apparatus including a plurality of oscillating transducers in a single hand-held probe.

BACKGROUND OF THE INVENTION

Ultrasonic transducers are used for a variety of applications which require different characteristics. For example, for abdominal imaging, high penetration is required. Therefore a 3½ MHz tranducer is a good choice. However, for more superfical imaging which is used where only up to 12 cm of penetration is required a 5 MHz transducer is a better choice.

It is well known in the prior art to use more than one transducer in a probe to cover a wide range of applications. In prior art systems, a plurality of transducers are mounted about a common axis and are continuously rotated past an ultrasound window to obtain the scanned data.

When two different transducers are mounted on such a rotating cylinder then the use of one of them at a time for imaging reduces the possible frame rate by a factor of 2. If three different transducers are mounted for rotation on the cylinder then the frame rate is reduced by a factor of three. Since high frame rates enable high quality dynamic imaging by the ultrasound system, it is a goal of experts in the field to provide more than one transducer in a single probe without reducing the frame rate.

Accordingly, an object of the present invention is to provide hand-held ultrasound probes having more than one transducer wherein means are provided so that imaging with the selected one of the multiple transducers is done at the same frame rate as with a probe having a single transducer.

BRIEF DESCRIPTION OF THE INVENTION

Accordingly, a multi-transducer hand-held ultrasound probe is provided, said probe comprises:
a housing having an ultrasound window,
means for positioning a selected one of said multi-transducers in front of said window,
means for oscillating said selected transducer in front of said window while activating said selected transducer to transmit and receive signals for imaging purposes.

A feature of the invention includes, rotating the plurality of transducers to position a selected transducer in front of the ultrasound window and then oscillating said selected transducer to obtain the scanned data.

A further feature of the invention comprises a unique drive mechanism for rotating and oscillating said transducers.

A related feature of the invention comprises the use of a specially constructed pulley system activated by a torquer for rotating and oscillating said selected transducer.

BRIEF DESCRIPTION OF THE DRAWING

The above mentioned and other objects and features of the invention will be best understood when considered in the light of the following description taken in conjunction with the accompanying drawings, wherein.

GENERAL DESCRIPTION

Figure 1:
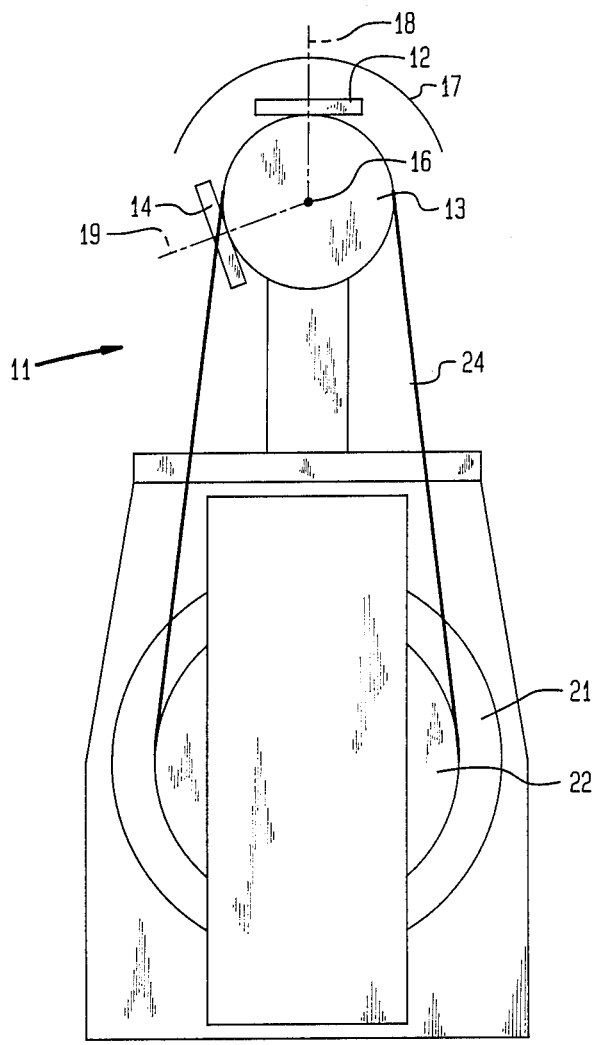
FIG. 1 is a sectionalized plan view of the inventive hand-held probe.

FIG. 1 shows a plan view of a hand-held probe 11 including a plurality of transducers. Two transducers are shown by way of example in FIG. 1, however, more than two transducers can be used within the scope of the invention. A first transducer 12 is shown mounted to a rotatable drum 13. The method of mounting is not important, it can be held by threaded fastners, clamping devices, or any well known mounting means. A second transducer 14 is also shown mounted to the drum 13. The drum is rotatable about an axis shown as 16.

The probe 11 includes an ultrasonic window 17 which enables the transfer of ultrasonic rays with a minimum of attenuation since the window is matched as closely as possible to the tissues of the human body; thereby, making the transfer of ultrasonic energy to and from the body as efficient as possible. The transducer 12 is shown as having an axis of symmetry of oscillation 18. Similarly, transducer 14 also has an axis of symmetry of oscillation 19.

Figure 2:
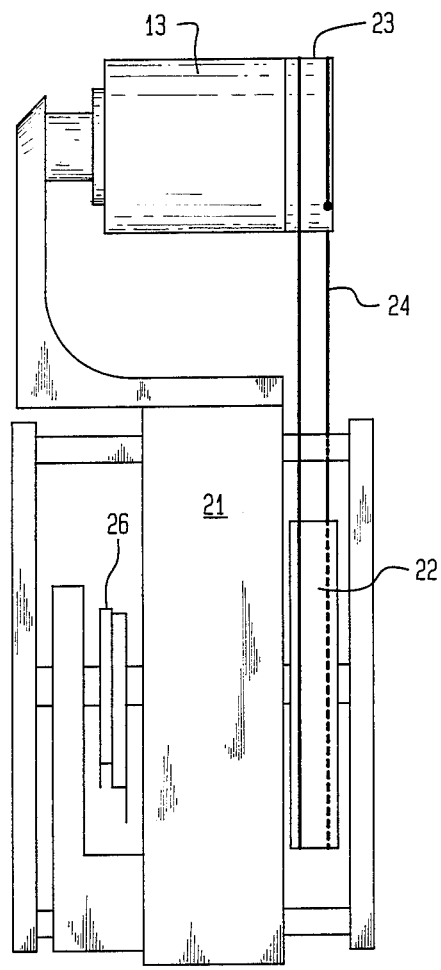
FIG. 2 is a sectional side view of the probe of FIG. 1.

Drive means are provided for rotating and oscillating drum 13. The drive means can be any drive means, however in a preferred embodiment a torquer, 21, is used. The torquer and the drum 13 are coupled together so that rotation provided by the torquer causes rotation of the drum. In a preferred embodiment the method of coupling is a pulley system. The pulley system (FIG. 2) includes a drive pulley 22 directly activated by the torquer 21. The driven pulley is shown as pulley 23 and is coupled to the drum 13. Means such as pulley cable 24 are provided for interconnecting pulleys 22 and 23.

Means such as sensor 26 are provided for sensing the angular position of the selected transducer. Actually the sensing is of the angular position of the drive pulley; however since the transducers are fixed to the drum the sensor means also indicates the angular position of the transducers 12 and 14.

The torquer in the preferred embodiment moves through 100 degrees that is plus or minus 50 degrees maximum. There is a 1 to 2 transmission ratio provided by the pulley system. The angular position sensor 26 is mounted to the torquer axis, therefore slippage of the cable 24 about either of the pulleys 22 or 23 is to be avoided.

Figure 3:
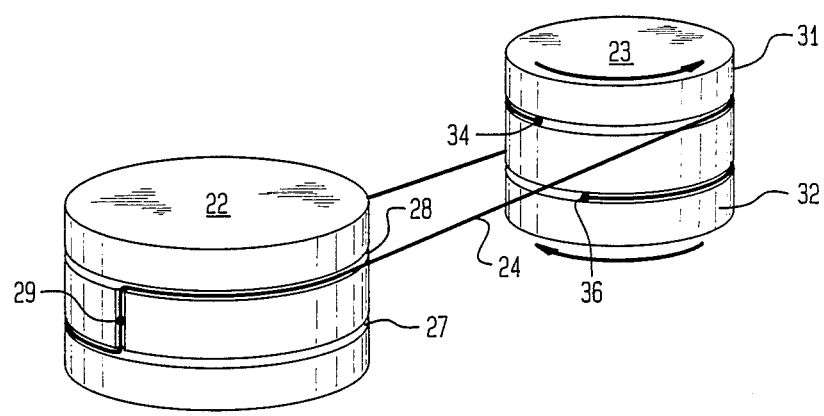
FIG. 3 is a more detailed showing of the pulley system for use in the hand-held probes of FIGS. 1 and 2.

Means are provided to acheive angular accuracy i.e. a no cable slippage system is required and such a pulley cable assembly is provided. More particularly pulley (FIG. 3) 22 includes a lower groove 27 and an upper groove 28. On the side of pulley 22 that is oppositely disposed from pulley 23 a cable attachment point 29 is provided. The cable is fixed to this point and goes from this point into the upper groove 28 and the lower groove 27, on opposite sides of the pulley.

Similarly, the pulley 23 is divided into two pulleys. More particularly, pulley 23 is divided into an upper pulley 31 and a lower pulley 32. The upper pulley, receives cable 24 from the upper grove 28 of pulley 22. This cable is attached to the upper pulley at point 34. Similarly the cable 24 coming from the lower grove 27 of pulley 22 is directed around lower pulley 32 where it is attached at point 36. Thus cable 24 is fixed to pulley 22 at a transfer point 29 where it is also directed from the upper grove 28 to the lower grove 27. The cable position extending from the upper groove is wrapped around pulley 31 of major pulley 23 and attached at point 34. The cable coming from the lower grove 27 is wrapped around pulley 32 and is attached at point 36.

This method of attaching the pulleys together to and from the cable pulley assembly enables the fixing of the cable to the pulley in a manner that practically eliminates all possibilities of slipping and still enables the rotation of the pulley 23 by more than 100 degrees.

Since the pulley can rotate more than 100 degrees it can position one of the plurality of transducers to be located in the center of ultrasonic windows so that its axis of symmetry of oscillation passes through approximately the mid-point of the window. Thus, in the example shown either the transducer 12, or transducer 14 is positioned to rotate around the axis 16 and to oscillate about it's axis of oscillating symmetry 18 or 19 respectively. Once the transducer is selected and positioned at the ultrasound window it oscillates and does not rotate. Thus, the frame rate is the same as a frame rate of a probe having only a single transducer.

While the invention has been described with regard to a broad aspect thereof it should be understood that the embodiment shown and described is an exlemplary embodiment only and not a limitation on the scope of the claims.

What is claimed is:

1. A multi-transducer ultrasound probe having multi-transducers comprising:
   a housing having an ultrasonic window,
   drum means having a plurality of transducers attached to the periphery thereof for use in positioning each transducer of said plurality of transducers in front of said window,
   rotating means for selectively rotating said drum means to align a selected one of said plurality of transducers with said window or for oscillating said selected transducer in front of said window while said selected transducer is activated to transmit and receive signals for imaging purposes,
   said rotating means rotating said drum means through non-slip pulley means,
   said non-slip pulley means comprising drive pulley means driven by said rotating means,
   said drive pulley means comprising a first and a second cable receiving groove,
   driven pulley means attached to said drum for selectively rotating or oscillating said drum means,
   cable means attaching said drive pulley means to said driven pulley means, said cable means surrounding each of said pulleys for less than 360 degrees,
   a transfer point comprising a threaded fastener located between said first and second grooves in said drive pulley means for fixedly attaching said cable means to be held in said first and second grooves of said drive pulley means,
   said driven pulley comprising a dual pulley sharing a common shaft and having first and second driven pulleys, said first and second driven pulleys being aligned with said first and second grooves, respectively,
   said cable means extending from said first cable receiving groove to said first pulley of said dual pulley and from said second cable receiving groove to said second pulley of said dual pulley, and
   means for affixing said cable means to said first pulley and to said second pulley.

2. The probe of claim 1 wherein said means for rotating comprises electric drive motor means.

3. The probe of claim 1 wherein said means for rotating includes non-slip pulley means.

4. The probe of claim 1 wherein said transfer point is positioned so that rotation of said drive pulley means can position each of said transducers in front of said window

* * * * *